United States Patent [19]

Sasaki

[11] Patent Number: 4,796,638
[45] Date of Patent: Jan. 10, 1989

[54] ARTIFACT DETECTING APPARATUS IN THE MEASUREMENT OF A BIOLOGICAL SIGNAL

[75] Inventor: Minoru Sasaki, Yokohama, Japan

[73] Assignee: Kabushiki Kaisya Advance Kaihatsu Kenkyujo, Tokyo, Japan

[21] Appl. No.: 169,144

[22] Filed: Mar. 10, 1988

Related U.S. Application Data

[63] Continuation of Ser. No. 876,859, May 22, 1986, abandoned.

[30] Foreign Application Priority Data

Sep. 28, 1984 [JP] Japan .................................. 59-201897

[51] Int. Cl.⁴ .............................................. A61B 5/04
[52] U.S. Cl. .................................... 128/696; 128/704
[58] Field of Search ............... 128/696, 901, 703, 704, 128/705, 706

[56] References Cited

U.S. PATENT DOCUMENTS 3,602,222  8/1971  Herndon ............................. 128/708
3,903,874  9/1975  Shakespeare ....................... 128/901
3,905,364  9/1975  Cudahy et al. ..................... 128/708
4,237,903  12/1980  Hofmann ............................ 128/708
4,478,224  10/1984  Bailey ............................... 128/901

Primary Examiner—Kyle L. Howell
Assistant Examiner—George Manuel
Attorney, Agent, or Firm—Finnegan, Henderson, Farabow, Garrett & Dunner

[57] ABSTRACT

An apparatus for detecting a high frequency artifact contained in an electrocardiogram signal is disclosed, which enables the presence of the high frequency artifact to be detected with a high precision by extracting high frequency components having a frequency and amplitude equal to or more than a predetermined value within a predetermined time interval of the input electrocardiogram signal by converting the high frequency components to pulses, by counting the pulses, and by comparing the counted pulses with the predetermined value. This apparatus is used in connection with, for example, an electrocardiograph, an electrocardiogram analyzer, and the like, and enables precise discrimination between an abnormal electrocardiogram waveform and the high frequency artifact.

4 Claims, 4 Drawing Sheets

ARTIFACT DETECTING APPARATUS IN THE MEASUREMENT OF A BIOLOGICAL SIGNAL

This application is a continuation, of application Ser. No. 876,859, filed May 22, 1986, and now abandoned.

TECHNICAL FIELD

The present invention relates to an artifact detecting apparatus in the measurement of a biological signal and, in particular, to an apparatus for discriminating the relatively high frequency noise (high frequency artifact) contained in an electrocardiogram signal from the natural electrocardiogram signal and for detecting the presence of the high frequency artifact with a high precision. The apparatus according to the present invention is used, for example, in connection with an elimination circuit for eliminating the high frequency artifact in an automatic electrocardiogram analyzer, a recognition stopping apparatus for the prevention of misrecognition in an arrhythmia recognition apparatus, and the like.

BACKGROUND ART

In general, an electrocardiogram is used in the diagnosis of cardiac diseases and recorded as a potential difference between the electrodes attached to the limb or chest, corresponding to the change of action potential accompanying a cardiac contraction. A typical electrocardiogram waveform is shown in FIG. 1. In the electrocardiogram waveform obtained through actual recording, there often appears a high frequency artifact AF occurring due to myoelectricity, the movement of electrodes and the like as shown in FIG. 2. Such a high frequency artifact frequently occurs, particularly in the long term electrocardiogram record which is the electrocardiogram recorded under the condition of living a routine life with a long term electrocardiograph attached to the body.

In the conventional diagnosis of cardiac diseases, a skilled examination engineer visually examines the electrocardiogram waveform, judges whether or not, for example, a portion R (hereinafter referred to as a R wave), having high frequency components occurs at an almost constant cycle, and determines the presence or absence of cardiac diseases based on the visual judgement.

When the amplitude level of the high frequency artifact is low, it is relatively easy to visually discriminate both an abnormal electrocardiogram waveform and a normal electrocardiogram waveform from the high frequency artifact. However, when the amplitude level of the high frequency artifact is approximate to that of the abnormal electrocardiogram waveform, it is difficult to exactly visually discriminate the former from the latter. Therefore, there has been a problem of misrecognition of the high frequency artifact as an abnormal electrocardiogram waveform, and it has been impossible to discriminate the former from the latter especially in the apparatus recognizing the electrocardiogram waveform electrically, such as an automatic analyzer and the like.

A prior art artifact detecting apparatus is described, for example in Japanese Unexamined Patent Publication (Kokai) No. 55-86444 or U.S. Pat. No. 3,905,364.

DISCLOSURE OF THE INVENTION

An object of the present invention is to provide an artifact detecting apparatus which enables the presence of the high frequency artifact to be detected with a high precision from an input electrocardiogram signal, and an abnormal electrocardiogram waveform to be discriminated exactly from the high frequency artifact in recognizing the abnormal electrocardiogram waveform.

According to the present invention, there is provided an artifact detecting apparatus comprising; a filter for extracting high frequency components from an input electrocardiogram signal; comparing and pulse-input generating means for comparing an amplitude voltage of the high frequency components with a preset first predetermined value and for generating a pulse when the amplitude voltage exceeds the first predetermined value; pulse-counting means for counting a pulse within a predetermined time interval from the comparing and pulse-generating means; and comparing and detecting means for comparing a value output from the pulse-counting means with a preset second predetermined value and for detecting an artifact based on the result of the comparison.

The artifact detecting apparatus according to the present invention detects the high frequency artifact based on the number of appearances of high frequency components (high frequency being defined as, for example, 100 Hz or more) existing in the arbitrary constant time interval of the electrocardiogram signal.

FIG. 3 shows a diagram for explaining the principle of artifact detection according to the apparatus of the present invention. In FIG. 3, (1), assuming that one cycle of the electrocardiogram signal is 1 (sec) and the time interval in which high frequency components are counted is 100 (msec), the count value of the high frequency components obtained from the electrocardiogram waveform is "3" because the portions at which the electrocardiogram signal has high frequency components are the Q wave, R wave, and S wave, and the time interval between Q wave and S wave is about 60 (msec). On the other hand, assuming that an abnormal electrocardiogram signal appears i.e., a block waveform as shown in FIG. 3, (2), the count value of the high frequency components obtained from the electrocardiogram waveform is "5" because the portions at which the electrocardiogram signal has high frequency components are the Q wave, R wave, A wave, B wave, and S wave. One example of the high frequency artifact is shown in FIG. 3, (3). In this case, the count value of the high frequency components obtained from the electrocardiogram waveform is "9", because this high frequency artifact has portions having nine high frequency components in the time interval of 100 (msec). Accordingly, it is possible to discriminate the high frequency artifact shown in FIG. 3, (3) from the electrocardiogram waveform by setting the critical number for the judgement for detecting the high frequency artifact to be at least "6".

In this case, the number for the judgement corresponds to the aforementioned first predetermined value and this first predetermined value is preferably set to a voltage value for detecting a portion having high frequency components in either the normal electrocardiogram signal or the abnormal electrocardiogram signal. This first predetermined value is a voltage value capable of detecting at least one voltage level of voltage levels corresponding to the points Q, R, and S, respectively, having high frequency components among the section points existing in the electrocardiogram, a voltage value capable of detecting the high frequency artifact having an amplitude voltage value which does not have an influence on the extraction of the section points necessary to the recognition of the abnormal electrocardiogram waveform, and a maximum value of the amplitude voltage under the consideration that if a T wave of the electrocardiogram signal has passed the filter it may have a relatively great amplitude.

On the other hand, the second predetermined value is preferably set to a value lying between a value output from the pulse-counting means corresponding to the last pulse of the largest pulses among the pulses generated within the predetermined time interval based on the comparison of the first predetermined value with the electrocardiogram signal having passed the filter and a value output from the pulse-counting means corresponding to the pulse preceding the last but one pulse.

According to the present invention, the high frequency artifact can be detected with a high precision by detecting high frequency components of the frequency equal to or more than the predetermined value within a predetermined time interval of the electrocardiogram signal, by counting the components, and by comparing this counted value with a predetermined threshold value.

BEST MODE FOR CARRYING OUT THE INVENTION

Figure 1:
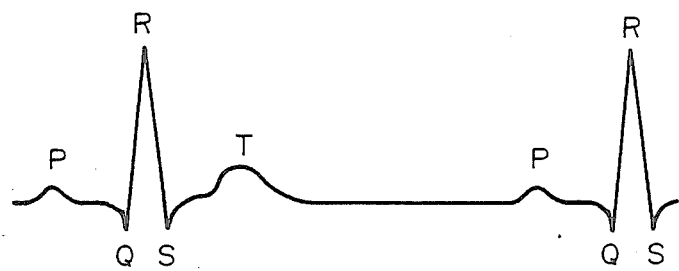
FIG. 1 is a diagram showing an electrocardiogram waveform.
Figure 2:
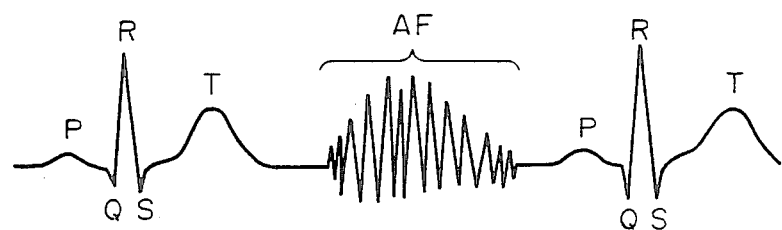
FIG. 2 is a diagram showing an electrocardiogram waveform accompanying a high frequency artifact.
Figure 3:
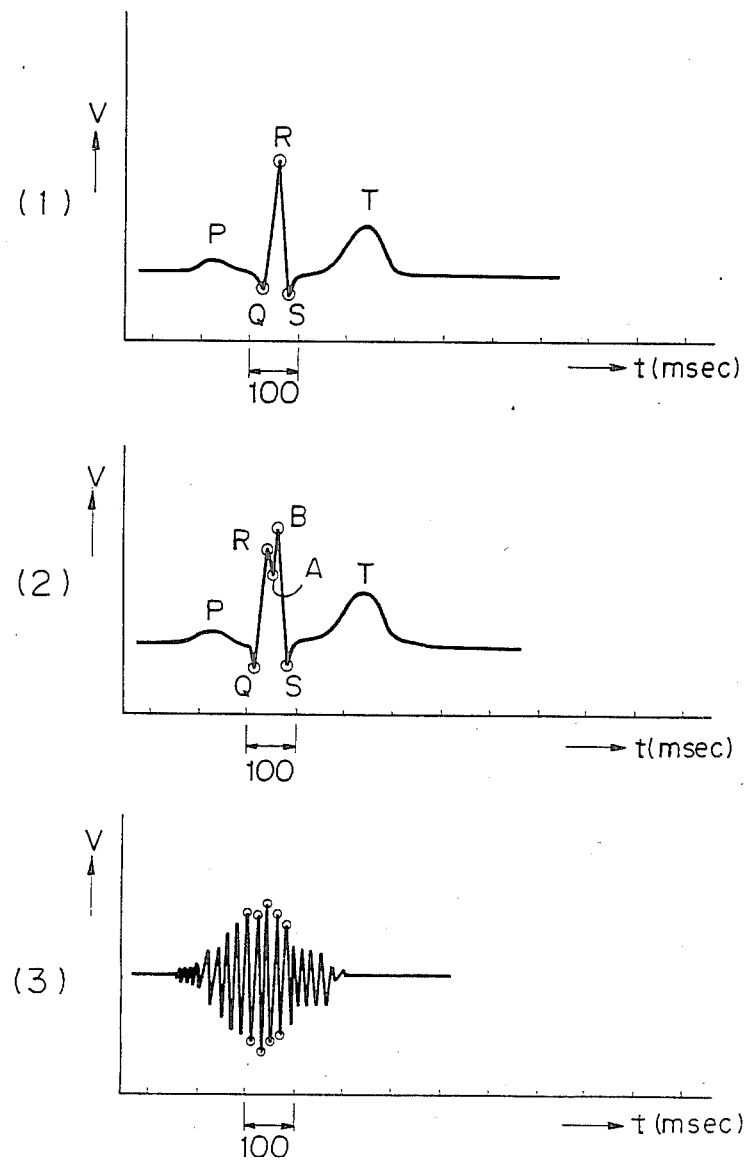
FIG. 3 is a diagram for explaining the principle of artifact detection according to the artifact detecting apparatus of the present invention.
Figure 4:
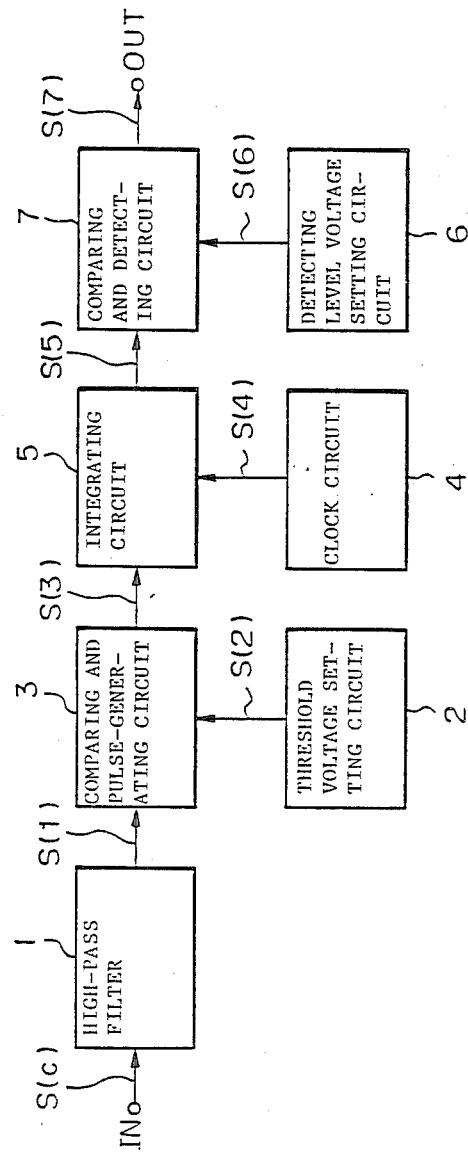
FIG. 4 is a block diagram showing one embodiment of the present invention, and, FIG. 5 is a diagram showing the signal waveform of each point in the apparatus shown in FIG. 4.
Figure 5:
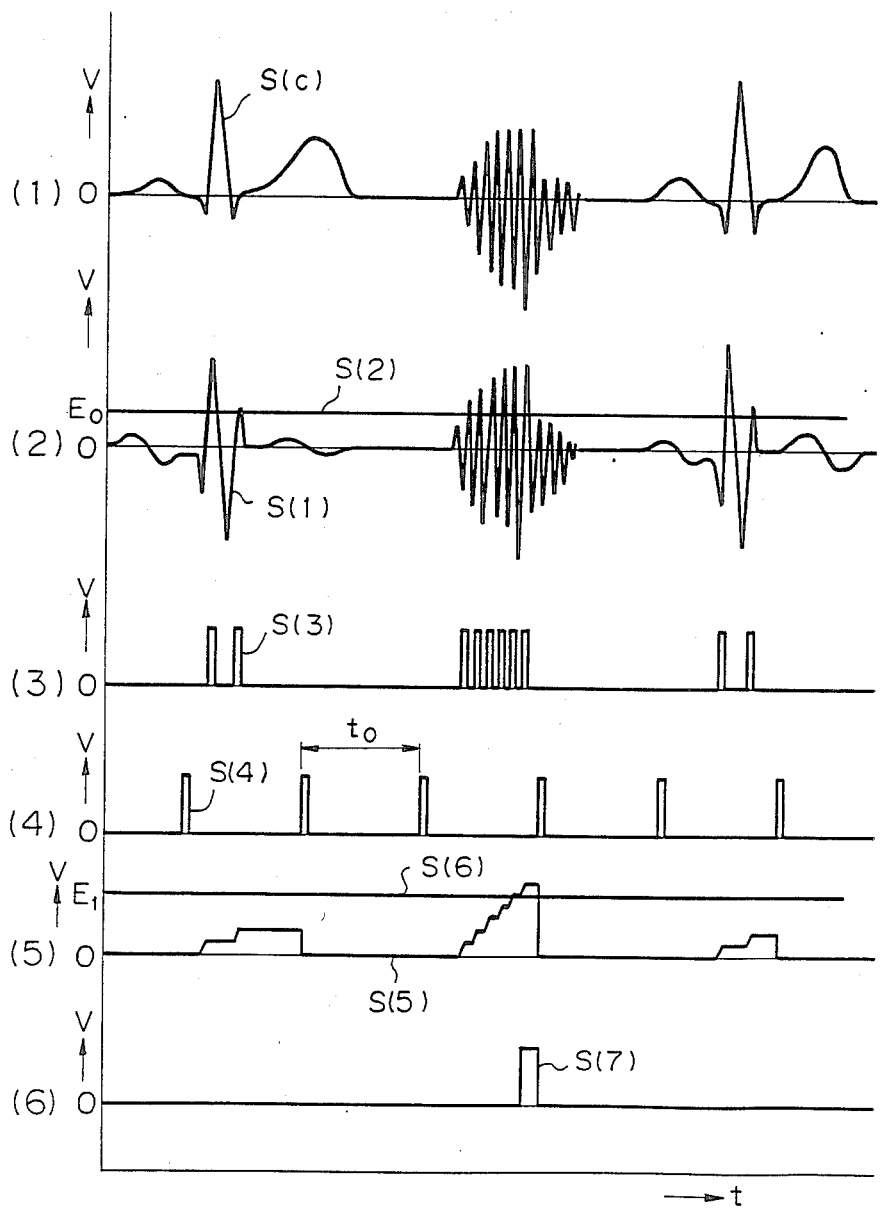

One embodiment of the artifact detecting apparatus according to the present invention is shown in FIG. 4, and the signal waveform of each point in the apparatus shown in FIG. 4 is shown in FIG. 5.

In FIG. 4, 1 is a high-pass filter. This high-pass filter 1 is provided for extracting only high frequency components from an electrocardiogram signal. 3 is a comparing and pulse-generating circuit. This comparing and pulse-generating circuit 3 is a circuit for converting into pulses an R wave of the normal electrocardiogram, an R wave distorted by the abnormal electrocardiogram due to ventricular extrasystole, and the like, and the high frequency artifact having the amplitude and frequency components approximately equal to an R wave of the normal electrocardiogram. That is to say, the comparing and pulse-generating circuit 3 is a circuit which compares the output signal S(1) voltage from the high-pass filter 1 with the output signal S(2) (threshold voltage $E_0$) from the threshold voltage setting circuit 2 and generates a pulse or pulses when the output signal S(1) voltage exceeds the threshold voltage $E_0$. The comparing and pulse-generating circuit 3 may be a Schmitt circuit as a concrete circuit.

Threshold voltage $E_0$ set in the threshold voltage setting circuit 2 is set to a voltage value capable of detecting at least one voltage level of a plurality of voltage levels corresponding to the points Q, R, and S, respectively, having high frequency components among the section points existing in the electrocardiogram, a voltage value capable of detecting the high frequency artifact having an amplitude voltage value which does not have an influence on the extraction of the section points necessary to the recognition of the abnormal electrocardiogram waveform, and a maximum value of the amplitude voltage under the consideration that a T wave of the electrocardiogram signal has passed the filter and may have a relatively great amplitude.

Integrating circuit 5 is a circuit for integrating the high frequency pulses obtained through the comparing and pulse-generating circuit 3. Clock circuit 4 generates a pulse S(4) at a predetermined time interval $t_0$ and resets the integrated output of the integrating circuit 5. 6 is a detecting level voltage setting circuit. The detecting level voltage $E_1$ is set in this detecting level voltage setting circuit 6. This detecting level voltage $E_1$ is set to a value lying between the integrated output voltage corresponding to the fifth pulse of the pulses input to the integrating circuit 5 and the integrated output voltage corresponding to the sixth pulse, for example, when the predetermined time interval $t_0$ of the pulse as shown in FIG. 5, (4) is 100 (msec). 7 is a comparing and detecting circuit. This circuit is a circuit for comparing the output signal S(5) voltage of the integrating circuit 5 with the output signal S(6) (detecting level voltage $E_1$) of the detecting level voltage setting circuit 6 and generating a pulse as an artifact detection signal S(7) at the output terminal OUT when the output signal S(5) voltage exceeds the detecting level voltage $E_1$.

This artifact detection signal S(7) can be used in the desired application and supplied to, for example, an elimination circuit for eliminating the high frequency artifact in an automatic electrocardiogram analyzer or a recognition stopping apparatus for the prevention of misrecognition in an arrhythmia recognition apparatus. For example, in the case of the elimination circuit of the high frequency artifact, the waveform portions at which the high frequency artifact occurs in the electrocardiogram waveform can be automatically eliminated and an electrocardiogram waveform free of the high frequency artifact can be obtained, based on the artifact detection signal from the comparing and detecting circuit 7.

The mode of operation of the artifact detecting apparatus constructed as mentioned above will be explained hereinafter. The electrocardiogram signal S(c) applied to the input terminal IN as shown in FIG. 5, (1) is input to the high-pass filter 1, where the low frequency components are removed, and the electrocardiogram signal S(1) as shown in FIG. 5, (2) is obtained. This electrocardiogram signal S(1) is input to the comparing and pulse-generating circuit 3 and compared with the threshold voltage $E_0$ from the threshold voltage setting circuit 2, where only the electrocardiogram signal having exceeded the threshold voltage $E_0$ is converted into the high frequency pulses S(3) having a single amplitude and a single pulse width as shown in FIG. 5, (3). The high frequency pulses obtained in the comparing and pulse-generating circuit 3 are input to the integrating circuit 5 and integrated. Then, the integrating circuit 5 is reset by the output pulse S(4) of the clock circuit 4 as shown in FIG. 5, (4), so that the waveform as shown in FIG. 5, (5) is obtained as the output signal S(5) of the integrating circuit 5. The output signal S(5) of the integrating circuit 5 is input to the comparing and detecting circuit 7 and compared with the preset detecting level voltage $E_1$. Based on this comparison, the artifact detection signal S(7) as shown in FIG. 5, (6) is obtained at the output terminal OUT as the output of the comparing and detecting circuit 7 when the output signal S(5) voltage of the integrating circuit 5 exceeds the detecting level voltage $E_1$. This artifact detection signal S(7) can be used in the desired application as aforementioned.

On the other hand, the electrocardiogram from the human organism is detected by means of at least the normal twelve leads. The normal twelve leads have a different waveform for each lead and include a lead having a positive R wave and a lead having a negative R wave. The phenomenon wherein the waveform differs for each lead occurs in the abnormal electrocardiogram waveform as well, and includes a lead having a positive R wave and a lead having a negative R wave. Therefore, the threshold voltage $E_0$ can be set as negative or as both positive and negative under the consideration of a lead having a negative R wave, although in the abovementioned embodiment only the case wherein the threshold voltage $E_0$ input to the comparing and pulse-generating circuit is positive is described. Such a change of the threshold voltage can be readily carried out by changing the value of each constituent element.

To the contrary, where the threshold voltage is set at only positive, the waveform obtained by converting a negative electrocardiogram waveform in the input signal to positive, a so-called absolute value waveform, may be generated by means of an inverter when the electrocardiogram signal is input to the comparing and pulse-generating circuit. This absolute value waveform is generally used in the electrocardiogram analyzer and is well known.

Also, in the cases that the above-mentioned absolute value waveform is input, that the Q wave and S wave of the normal electrocardiogram have the possibility of being simultaneously detected as the high frequency pulse, that there is a lead in which the Q wave and S wave have a relatively great amplitude, and the like, there is a possibility that the number of the high frequency pulses in the normal electrocardiogram waveform and abnormal electrocardiogram waveform will exceed the threshold "6" of the number of the aforementioned high frequency pulses. Therefore, in order to prevent this, both the setting of the threshold voltage $E_0$ input to the comparing and pulse-generating circuit and the change of the setting of the detecting level voltage $E_1$ input to the comparing and detecting circuit are changed.

Furthermore, in the above-mentioned embodiment the integrating circuit is used as the means for counting pulses output from the comparing and pulse-generating circuit. However, the means is not restricted to the integrating circuit and may be a counting circuit such as a binary counter which performs a comparison according to the sequence number.

Moreover, in the above-mentioned embodiment the threshold voltage $E_0$ is set so that the high frequency amplitude voltage of Q, R and S wave can be detected, the predetermined time interval $t_0$ is set to contain the high frequency components of the Q, R, and S waves, and the detecting level voltage $E_1$ is set to a detecting level under the consideration of the high frequency components of arrhythmia. However, the values of the threshold voltage $E_0$, the predetermined time interval $t_0$, and the detecting level voltage $E_1$ are not restricted to the above-mentioned. For example, the precision of discrimination of the high frequency artifact can be improved by setting the threshold voltage $E_0$ so that only the high frequency amplitude voltage of the R wave can be detected, by setting the predetermined time interval $t_0$ to a shorter interval, and by setting the detecting level voltage $E_1$ to a value under the consideration of only the high frequency components of the R wave. Accordingly, the detection of the high frequency artifact can be carried out by appropriately selecting the respective value independently of or dependently on each other according to the purpose of diagnosis.

I claim:

1. An artifact detecting apparatus comprising:
   a filter for passing high frequency components approximate to or the same as the frequency components of a QRS wave complex signal contained in a electrocardiogram signal;
   a first comparing means for comparing each of the amplitude voltages of said high frequency components with a first predetermined level and for generating a pulse or pulses when at least one voltage of said amplitude voltages exceeds said predetermined level;
   pulse-counting means for counting a pulse or pulses output from said first comparing means within a predetermined time interval; and
   a second comparing means for comparing a level of a signal output from said pulse-counting means with a second predetermined level and for output in a signal indicating a detection of an artifact when said level exceeds said second predetermined level.

2. Apparatus as set forth in claim 1, wherein said first predetermined level is set to a level exceeding at least one voltage level of a plurality of voltage levels corresponding to section points having said high frequency components contained in said electrocardiogram signal.

3. Apparatus as set forth in claim 1, wherein said second predetermined level is set to a level between a level of a signal generated in said pulse-counting means in response to the last pulse among the greatest number of pulses output from said first comparing means within said predetermined time interval and a level of a signal generated in said pulse-counting means in response to the pulse preceding said last pulse by one pulse.

4. Apparatus as set forth in claim 1, wherein said pulse-counting means comprises a circuit for integrating a pulse or pulses output from said first comparing means and for outputting a signal corresponding to a vlaue integrated within said predetermined time interval.

* * * * *